US009689840B2

(12) United States Patent
Berkelman et al.

(10) Patent No.: US 9,689,840 B2
(45) Date of Patent: Jun. 27, 2017

(54) CONJUGATES OF 1,4,7-TRIAZACYCLONONANES, DINUCLEAR METAL COMPLEXES OF SUCH CONJUGATES, AND METHODS OF USE FOR BOTH 1,4,7-TRIAZACYCLONONANES AND CONJUGATE

(71) Applicant: Bio-Rad Laboratories, Inc., Hercules, CA (US)

(72) Inventors: Thomas R. Berkelman, Oakland, CA (US); Lisandra Martin, Victoria (AU); Rhiannon Jones, Victoria (AU); John Walker, II, San Leandro, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 0 days.

(21) Appl. No.: 15/015,415

(22) Filed: Feb. 4, 2016

(65) Prior Publication Data
US 2016/0223491 A1    Aug. 4, 2016

Related U.S. Application Data

(62) Division of application No. 13/973,596, filed on Aug. 22, 2013, now Pat. No. 9,274,103, which is a division of application No. 13/044,220, filed on Mar. 9, 2011, now Pat. No. 8,536,162.

(60) Provisional application No. 61/368,106, filed on Jul. 27, 2010, provisional application No. 61/314,431, filed on Mar. 16, 2010.

(51) Int. Cl.
*C07D 255/02* (2006.01)
*G01N 27/447* (2006.01)
*C08F 220/60* (2006.01)
*G01N 33/543* (2006.01)
*C07F 3/06* (2006.01)
*C07F 13/00* (2006.01)
*C08F 220/56* (2006.01)
*B01D 15/38* (2006.01)

(52) U.S. Cl.
CPC ..... *G01N 27/44747* (2013.01); *C07D 255/02* (2013.01); *C07F 3/06* (2013.01); *C07F 13/005* (2013.01); *C08F 220/56* (2013.01); *C08F 220/60* (2013.01); *G01N 33/54306* (2013.01); *B01D 15/3823* (2013.01); *Y10T 436/143333* (2015.01); *Y10T 436/163333* (2015.01)

(58) Field of Classification Search
None
See application file for complete search history.

(56) References Cited

U.S. PATENT DOCUMENTS 7,456,276 B2    11/2008    Christensen et al.
8,536,162 B2    9/2013    Berkelman et al.
9,274,103 B2    3/2016    Berkelman et al.

FOREIGN PATENT DOCUMENTS

JP    11-061187 A    3/1999
WO    03/042249    *    5/2003    ............. C08B 37/00

OTHER PUBLICATIONS

Brudenell, et al., "Structural, EPR, and Electrochemical Studies of Binuclear Copper(II) Complexes of Bis(pentadentate) Ligands Derived from Bis(1,4,7-triazacyclonane) Macrocycles," *Inorg. Chem*, vol. 37, pp. 3705-3713 (1998).
Brudenell, et al., "Structural, spectroscopic and electrochemical studies of binuclear nickel(II) complexes of bis(pentadentate) ligands derived from bis(14,7-triazacyclonanane) macrocycles," *J Chem Soc,, Dalton Trans.* pp. 3919-3925 (1998).
Brudenell, et al., "Solution and solid state structures of binuclear zinc(II) complexes of bis(pentadentate) ligands derived from bis(1,4,7-triazacyclonane) macrocycles," *J Chem Soc, Dalton Trans.*, pp. 1475-1481 (1999).
Brudenell, et al., "Structural, Spectroscopic, and Electrochemical Studies of Binuclear Manganese(II) Complexes of Bis(pentadentate) Ligands Derived from Bis(1,4,7-triazacyclononane) Macrocycles," *Inorg. Chem.*, vol. 39(5), pp. 881-892 (2000).
Iranzo, et al., "Physical and Kinetic Analysis of the Cooperative Role of Metal Ions in Catalysis of Phosphodiester Cleavage by a Dinuclear Zn(II) Complex," *J. Am. Chem. Soc.*, vol. 125, pp. 1988-1993 (2003).
Iranzo, et al., "Cooperativity between Metal Ions in the Cleavage of Phosphate Diesters and•RNA by Dinuclear Zn(II) Catalysts," *Inorg Chem.*, vol. 42(24), pp. 7737-7746 (2003).
O'Donoghue, et al., "Substrate Specificity of an Active Dinuclear Zn(II) Catalyst for Cleavage of RNA Analogues and a Dinucleoside," *J. Am. Chem. Soc.*, vol. 128, pp. 1615-1621 (2006).
Sessler, et al., "Oxo-Brldged Iron Clusters. Synthesis of 1,3-Bis(1,4,7-triaza-1-cyclononyl)-2-hydroxypropane and Its Stabilization of the $Fe_4O_6$, Core," *Inorg Chem.*, vol. 32(20)., pp. 4277-4283 (1993).
Office Action in Chinese Application No. 201180019190.6, dated Dec. 6, 2013.
Office Action dated Mar. 19, 2014 in Japanese application No. 2013-500088.

* cited by examiner

*Primary Examiner* — Noble Jarrell
(74) *Attorney, Agent, or Firm* — Kilpatrick, Townsend & Stockton LLP

(57) ABSTRACT

Conjugates of 1,3-bis(1,4,7-triazacyclonon-1-yl)-2-hydroxypropanes with a variety of conjugating members are used in the formation of dinuclear metal complexes which bind to phosphate esters. By virtue of their conjugated forms, the complexes are incorporated into chromatographic media, affinity binding reagents, and dyes, which make the complexes useful in a wide range of assays, separations, and purifications. In addition, dinuclear metal complexes of 1,3-bis(1,4,7-triazacyclonon-1-yl)-2-hydroxypropanes that are not so conjugated are used in the detection of phosphate esters of biological species by either MALDI-TOF mass spectrometry or by dye displacement.

14 Claims, No Drawings

CONJUGATES OF 1,4,7-TRIAZACYCLONONANES, DINUCLEAR METAL COMPLEXES OF SUCH CONJUGATES, AND METHODS OF USE FOR BOTH 1,4,7-TRIAZACYCLONONANES AND CONJUGATE

CROSS-REFERENCE TO RELATED APPLICATIONS

This application is a divisional of U.S. application Ser. No. 13/973,596 filed Aug. 22, 2013 which is a divisional of U.S. application Ser. No. 13/044,220 filed Mar. 9, 2011 which claims the benefit of U.S. Provisional Applications No. 61/368,106 filed Jul. 27, 2010, and U.S. Provisional Application No. 61/314,431, filed Mar. 16, 2010, each of which is incorporated in its entirety herein for all purposes.

BACKGROUND OF THE INVENTION

Phosphorylation and dephosphorylation are metabolically significant reactions in physiological systems. These reactions occur at hydroxyl groups of certain proteins, at nitrogen atoms of certain other proteins, and at carboxyl groups of still more proteins, in each case having an effect on the activity and function of these proteins in vivo. Certain phosphorylation/-dephosphorylation reactions are mediated by protein kinases and phosphatases and their occurrences provide an indication of the activity of these enzymes. Abnormalities in phosphorylation/dephosphorylation reactions have been implicated in cell carcinogenesis, in allergic disorders, and in Alzheimer's disease. Protein phosphorylation is an essential process in all living cells, for signal transduction, apoptosis, proliferation, differentiation, and metabolism. Methods for the determination of the phosphorylation status of proteins are thus valuable in exploring the molecular origins of diseases and in the design of new drugs.

Certain metalloenzymes that contain two metal ions are known to catalyze dephosphorylation reactions, in particular the hydrolysis of phosphate diesters. Studies of the mechanism by which these reactions occur have involved the use of synthetic organic ligands that form dimetallic complexes and perform the same catalytic function. Most of these synthetic ligands were found to have low solubility in water, however, which limited their utility in laboratory studies. To remove this obstacle, a water-soluble ligand, 1,3-bis(1,4,7-triazacyclonon-1-yl)-2-hydroxypropane, has been developed. Disclosures of Zn(II) complexes of this ligand and its use in the hydrolysis of RNA are published by Iranzo, O., et al., "Cooperativity between Metal Ions in the Cleavage of Phosphate Diesters and RNA by Dinuclear Zn(II) Catalysts," *Inorganic Chemistry* 42(24), 7737-7746 (2003), and Iranzo, O., et al., "Physical and Kinetic Analysis of the Cooperative Role of Metal Ions in Catalysis of Phosphodiester Cleavage by a Dinuclear Zn(II) Complex," *J. Am. Chem. Soc.* 125(7), 1988-1993 (2003). Further studies of this molecule and of the transition state that it forms with the phosphate esters are reported by Yang, M.-Y., et al., "Substrate specificity for catalysis of phosphodiester cleavage by a dinuclear Zn(II) complex," *Chem. Commun.* 2003, 2832-2833, and Yang, M.-Y., et al., "A transition state analog for phosphate diester cleavage catalyzed by a small enzyme-like metal ion complex," *Bioorganic Chemistry* 35, 366-374 (2007).

SUMMARY OF THE INVENTION

In part, the present invention resides in conjugates of substituted or unsubstituted 1,3-bis(1,4,7-triazacyclonon-1-yl)-2-hydroxypropanes with a variety of conjugating members, each conjugate capable of forming a dimetallic complex in the same manner as the complexes disclosed in the reports cited above. The invention also resides in functionalized 1,3-bis(1,4,7-triazacyclonon-1-yl)-2-hydroxypropanes, substituted or unsubstituted, the functional groups of which are reactive with a conjugating member. The substituted or unsubstituted 1,3-bis(1,4,7-triazacyclonon-1-yl)-2-hydroxypropanes are referred to for convenience herein as "ligands," and the conjugates are those ligands that are conjugated with a conjugating member that serves one of a variety of additional functions as described below. The invention further resides in the dinuclear metal complexes of these conjugates, and in various uses of these complexes other than in the hydrolysis of phosphate diesters. The utility of each complex arises from the particular conjugating member used in forming the conjugate, in conjunction with the phosphate-binding activity of the two metal ions.

The present invention further resides in methods for detecting phosphate esters in a sample by MALDI-TOF (Matrix-Assisted Laser Desorption/Ionization Time-of-Flight) mass spectrometry, using either dinuclear metal complexes of the ligands or dinuclear metal complexes of the conjugates of the ligands, by mixing such a complex with the sample in a suitable matrix to form positively charged dinuclear metal complexes of the phosphate esters. When the mass spectrometry scan is run on the sample and matrix, the differentiation of the positively charged dinuclear metal complexes of phosphate esters in the sample from uncomplexed components is increased due to the additional mass imparted by the ligand in the complex as well as a change in the charge of the complex. Ligands that are not conjugated are of particular interest in this aspect of the invention.

A still further aspect of the invention resides in methods for detecting phosphate esters in a sample by dye displacement, again using either dinuclear metal complexes of the ligands or dinuclear metal complexes of the conjugates of the ligands. In this aspect of the invention, the dinuclear metal complexes are further complexed with a chromophoric compound that has two key characteristics—(1) the chromophoric compound has a lower affinity to the metal-charged ligand (or conjugate of the ligand) than do the phosphate esters, i.e., the phosphate esters bind more strongly to the ligand and will displace the chromophoric compound in the complex upon contact; and (2) the chromophoric compound has a different absorbance or fluorescence spectrum when bound than when unbound. One example of a chromophoric dye that meets this description is pyrocatechol violet. The spectral change that occurs as a result of the displacement of the chromophoric compound from the complex by the phosphate esters thus serves as an indication of the presence of the phosphate esters in the sample. In this aspect of the invention as well, the use of an unconjugated ligand is of particular interest.

DETAILED DESCRIPTION OF EMBODIMENTS OF THE INVENTION

The ligands, which are substituted or unsubstituted 1,3-bis(1,4,7-triazacyclonon-1-yl)-2-hydroxypropane, are represented by generic Formula (I):

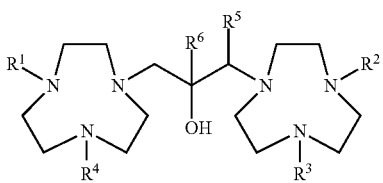

(I)

In Formula (I), the groups $R^1$, $R^2$, $R^3$, $R^4$, $R^5$, and $R^6$ are the same or different (some the same and others different) and are either H or a lower alkyl group. The expression "lower alkyl" is defined as an alkyl group of six carbon atoms or less. Preferred groups for $R^1$ through $R^6$ are either H, $C_1$-$C_3$ alkyl, or combinations selected from H and $C_1$-$C_3$ alkyl, and the most preferred is H. The term "substituted" in this context denotes that one or more of $R^1$, $R^2$, $R^3$, $R^4$, and $R^6$ is an alkyl group rather than an H atom.

Ligands that are described herein as not being conjugated are those in which $R^1$, $R^2$, $R^3$, $R^4$, $R^5$, and $R^6$ are the same or different and each is either H or a lower alkyl group. The conjugates of the ligands are those compounds of Formula (I) in which a conjugating member occupies any of the positions indicated by $R^1$, $R^2$, $R^3$, $R^4$, $R^5$, and $R^6$, through a linking group joining the conjugating member to the remainder of the structure. Any such R groups that do not represent the conjugating member are either H or a lower alkyl group, as indicated above. For the conjugates, one or more of $R^1$ through $R^6$ is thus -L-$R^7$, where L represents the linking group and $R^7$ is the conjugating member, and the remaining group(s) of $R^1$ through $R^6$, which are either the same or different (some the same and others different), are each either H or $C_1$-$C_6$ alkyl. For the functionalized ligands, one or more of $R^1$ through $R^6$ is -L', where L' represents the unreacted linking group that is reactive with the conjugating member. In the functionalized ligands as in the conjugates, the remaining group(s) of $R^1$ through $R^6$, which are either the same or different (some the same and others different), are each either H or $C_1$-$C_6$ alkyl. In preferred functionalized ligands or conjugates, only one of $R^1$ through $R^6$ is -L' or -L-$R^7$, respectively, and in further preferred ligands or conjugates, only $R^5$, only $R^6$, or only $R^2$ is -L' or -L-$R^7$. Of the $R^1$ through $R^6$ groups that are not replaced by -L' or -L-$R^7$, such groups are preferably either H, $C_1$-$C_3$ alkyl, or combinations selected from H and $C_1$-$C_3$ alkyl, and the most preferred is H. The conjugating member $R^7$ is either an acrylamide group, a fluorescent dye, an affinity-type binding member, or a solid chromatographic support. The linking group L' or L is any conventional linker with two binding sites, one of which forms a covalent bond with the conjugating member $R^7$ and the other forms a covalent bond with the adjacent carbon atom on the remainder of Formula (I). The linking group generally has from 3 to 30 atoms selected from C, N, O, P, and S, in addition to hydrogen atoms filling available valences, and is either cyclic, acyclic, aromatic or a combination of cyclic, acyclic, and aromatic moieties. Examples of linking groups are amine alkyl linkages, alkenyl linkages, amide or amide-containing linkages, ester or ester-containing linkages, and ether or ether-containing linkages. Preferred linking groups for L' are —($C_1$-$C_4$ alkyl)-$NH_2$, —($C_1$-$C_4$ alkyl)-C(=O)—$NH_2$, —($C_1$-$C_4$ alkyl)-NH—$CO_2$H, —($C_1$-$C_4$ alkyl)-C(=O)—NH—($C_1$-$C_4$ alkyl)-$NH_2$, and —($C_1$-$C_4$ alkyl)-NH—C(=O)—($C_1$-$C_4$)—$NH_2$, and particularly preferred are —$CH_2CH_2$—NH—, —$CH_2$—C(=O)—$NH_2$, —$CH_2CH_2$—NH—$CO_2$H, —$CH_2$—C(=O)—NH—$CH_2CH_2$—$NH_2$, and —$CH_2CH_2$—NH—C(=O)—$CH_2CH_2$—$NH_2$. Preferred groups for L are ($C_1$-$C_4$ alkyl)-C(=O)—NH—($C_1$-$C_4$ alkyl)-, —($C_1$-$C_4$ alkyl)-NH—C(=O)— ($C_1$-$C_4$ alkyl)-NH—, and —($C_1$-$C_4$ alkyl)-NH—, and particularly preferred are —$CH_2$—C(=O)—NH—$CH_2$—$CH_2$—, —$CH_2$—$CH_2$—NH—C(=O)— $CH_2$—$CH_2$—NH—, and —$CH_2$—$CH_2$—NH—.

When $R^7$ is an acrylamide group, -L-$R^7$ is preferably —$CH_2$—C(O)—NH—$(CH_2)_n$NH—C(O)—CH=$CH_2$ or —$(CH_2)_2$—NH—C(O)—$(CH_2)$—NH—C(O)—CH=$CH_2$ where n is 1 to 6, and the most preferred are —$CH_2$—C(O)—NH—$(CH_2)_2$—NH—C(O)—CH=$CH_2$ and —$(CH_2)_2$—NH—C(O)—$(CH_2)_2$—NH—C(O)—CH=$CH_2$. When this particular -L-$R^7$ replaces $R^5$ and the remaining R's are all H, the conjugate has the formula

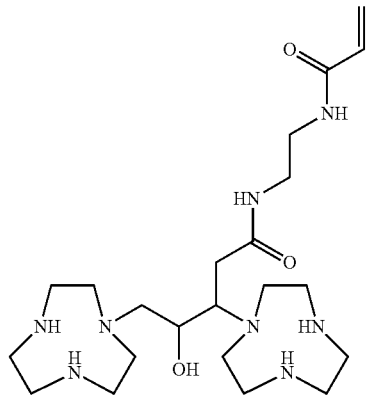 [SMILES: C=CC(=O)NCCNC(=O)CC(C(O)CN1CCNCCNCC1)N1CCNCCNCC1]

Functionalized polyacrylamide gels can be formed from conjugates and dinuclear metal complexes in accordance with this invention where the conjugating member is acrylamide. The functional group in these gels is the dimetal complex of the acrylamide-containing conjugate, and the resulting gels can be used for electrophoretic separations of phosphate monoesters of proteins, peptides, or nucleic acids from the non-phosphorylated forms of these species. Phosphate monoesters of proteins, peptides, or nucleic acids within the mixture will migrate more slowly during electrophoresis due to interaction between the phosphate esters and the dimetal complex functional groups on the gels. Phosphorylated components of the mixture can thereby be distinguished from their unphosphorylated counterparts. The functionalized gel is formed by including the dimetal complex in the monomer mixture, which will generally also include non-functionalized acrylamide, a crosslinker, and an initiator. Suitable crosslinkers and initiators are well known in the art. Examples of crosslinkers are bisacrylamide and ethylene diacrylate, and examples of initiators are riboflavin, ammonium persulphate, and tetramethylethylenediamine (TEMED). The conditions for polymerization of the monomers and the concentrations of the various components of the monomer mixture are the same as those used in procedures of the prior art for the formation of the polyacrylamide gels.

Dinuclear metal complexes of the ligands of Formula (I) for use in the practice of this invention are those having Formula (II):

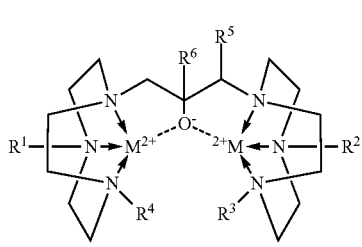

(II)

In Formula (II), $R^1$ through $R^6$ are as defined above, and M is a divalent metal. A preferred group of divalent metals is Ca, Zn, Cr, Mn, Fe, Co, Ni, and Cu (all in divalent form). Particularly preferred divalent metals are Zn(II) and Mn(II).

When used in the various methods of the present invention, the dinuclear metal complexes of Formula (II) form phosphate association complexes of Formula (III):

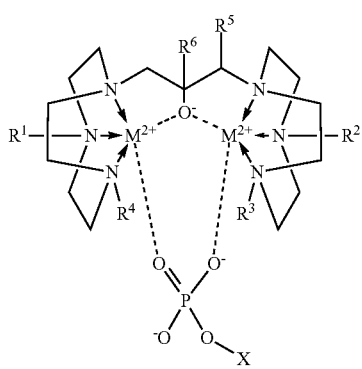

(III)

In Formula (III), X is the residue of a peptide, protein, nucleic acid, or in general any species to which the complexes of this invention are to be applied for any of the various purposes stated herein.

When $R^7$ is a fluorescent dye, the dye can be any of the variety of fluorescent dyes known for use in the labeling of biological species. Examples are:

fluorescein and fluorescein derivatives such as fluorescein isothiocyanate, rhodamine derivatives such as tetramethyl rhodamine, rhodamine B, rhodamine 6G, sulforhodamine B, rhodamine 101 (Texas Red), and rhodamine 110, 4,4-difluoro-4-bora-3a,4a-diaza-s-indacene (BODIPY) and derivatives thereof, pyrenes and pyrene derivatives such as 8-methoxypyrene-1,3,6-trisulfonic acid, pyridyloxazole derivatives, dapoxyl derivatives, umbelliferone, 1-anilino-8-naphthalenesulfonic acid, 3,6-disulfonate-4-amino-naphthalimide, tri-, penta-, and heptamethine cyanine dyes, and luminescent transition metal complexes such as tris(2,2'-bipyridine)ruthenium(II) or cyclometalated complexes of Ir(III).

When $R^7$ is tetramethyl rhodamine, for example, -L-$R^7$ is preferably

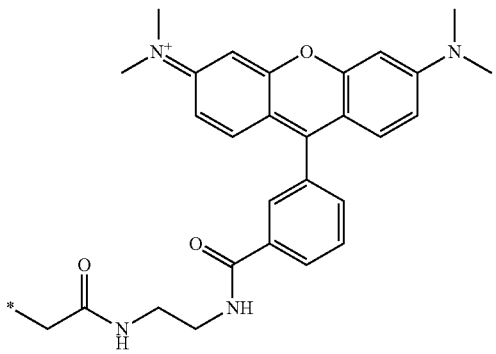 [SMILES: *CC(=O)NCCNC(=O)c1cccc(-c2c3ccc(=[N+](C)C)cc-3oc3cc(N(C)C)ccc23)c1]

where the asterisk denotes the site of attachment to the 1,3-bis(1,4,7-triazacyclonon-1-yl)-2-hydroxypropane.

When this linker and dye replace $R^5$ and $R^1$ through $R^4$ are all H, the resulting conjugate has the formula

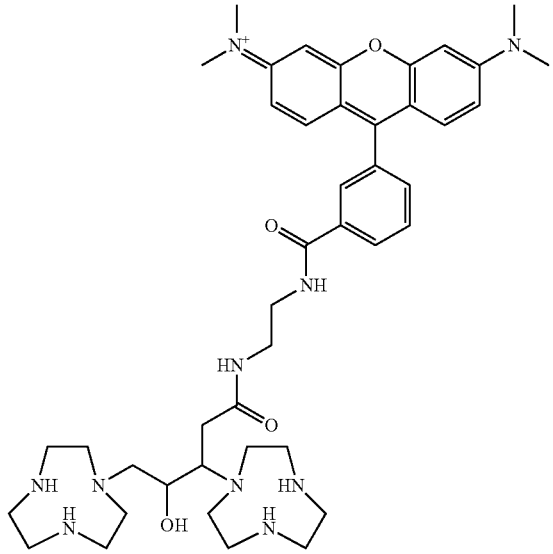 [SMILES: CN(C)c1ccc2c(-c3cccc(C(=O)NCCNC(=O)CC(C(O)CN4CCNCCNCC4)N4CCNCCNCC4)c3)c3ccc(=[N+](C)C)cc-3oc2c1]

Dinuclear metal complexes in accordance with this invention that are formed from conjugates containing fluorescent dyes can be used for the staining of gels or blots to identify and quantify phosphate esters, such as phosphoproteins, for example, in samples of biological fluids and in assay media in general.

When $R^7$ is an affinity-type binding member, examples of such binding members are biotin, avidin, streptavidin, antibodies, and antibody fragments. When $R^7$ is biotin, -L-$R^7$ is preferably

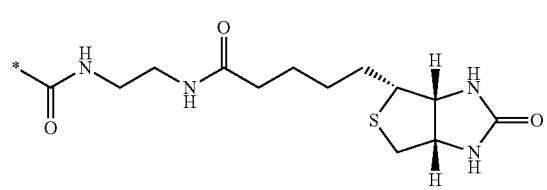 [SMILES: *C(=O)NCCNC(=O)CCCC[C@H]1SC[C@H]2NC(=O)N[C@H]21]

where the asterisk denotes the site of attachment to the 1,3-bis(1,4,7-triazacyclonon-1-yl)-2-hydroxypropane.

When this functional group replaces $R^5$ and $R^1$ through $R^4$ are all H, the resulting conjugate has the formula

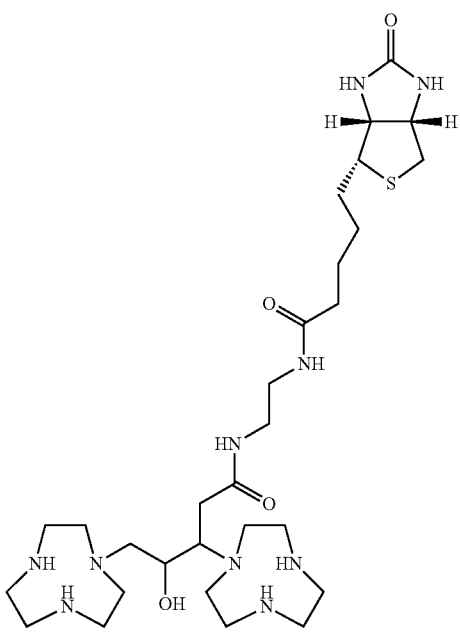 [SMILES: O=C(CCCC[C@H]1SC[C@H]2NC(=O)N[C@H]21)NCCNC(=O)CC(C(O)CN1CCNCCNCC1)N1CCNCCNCC1]

Dinuclear metal complexes in accordance with this invention in which $R^6$ is an affinity binding member are useful in the detection of phosphoproteins and other phosphate esters bound to or otherwise immobilized on a solid support. The ability of the affinity binding member to bind with specificity to a second affinity binding member to form an affinity binding pair allows the attachment of a reporter group to the complexes through the binding pair, either before or after the complexes have associated with the phosphate esters. This allows detection by any type of reporter group that can be conjugated to an affinity binding member. Affinity binding pairs are well known; examples are biotin and avidin, biotin and streptavidin, and any of various antibodies or antibody fragments and antigens. Examples or reporter groups are radioactive labels, chemiluminescent labels, and enzymes. Examples of enzymes are horseradish peroxidase, chloramphenicol acetyl transferase, β-galactosidase, alkaline phosphatase, and luciferase. To illustrate the use of dinuclear metal complexes containing an affinity binding member, the solid support, such as for example, a blotting membrane, on which the phosphate esters have been captured is first contacted with the complex. If, for example, the conjugating member on the complex is biotin, the support is contacted with a streptavidin-enzyme conjugate. This is followed by incubation of the support with an enzyme substrate and detection of the change, most often a color change, in the substrate, mediated by the enzyme. Optimal conditions for the contact and incubation are readily apparent to those of skill in the art.

When $R^7$ is a solid chromatographic support, the term "solid" is used herein to include semi-solids such as gels, flexible solids such as membranes and films, and rigid solids such as those used in the formation of incompressible beads, granules, and column or tube walls. Examples of such solids are polyacrylamide, crosslinked silicon polymers, silica gel, agarose, polyvinyl alcohols, cellulose and nitrocellulose. A chromatographic support bearing the dinuclear metal complexes of this invention can be used to extract phosphorylated compounds (phosphate esters) from fluids such as biological fluids, assay media, or any fluids containing phosphorylated compounds, for purposes of purification or enrichment.

Conjugates in accordance with this invention can be prepared by conventional procedures, beginning with 1,4,7-triazacyclononane derivatives with one or more of the secondary amine groups protected either with a suitable protecting group or by formation of a 1,4,7-triazacyclononane tricyclic orthoamide. Appropriate functional groups can be selectively placed in one or more of the unprotected $R^1$ through $R^4$ positions. An appropriate functional group can also be placed in the $R^5$ position by selection of an appropriate synthetic intermediate that will join the two 1,4,7-triazacyclononane groups by connecting one ring nitrogen from each macrocycle with a three-carbon chain. The choice of functional group will vary with the choice of linking group and with the means by which the linking group is attached, such attachment being achievable by any of the wide range of linking reactions known in the art. Prominent example of functional groups are carboxylic acids or esters of carboxylic acids that can react with an amine functionality appended to the conjugating member, or an amine group that can react with an active carboxylic acid ester or acid chloride, both resulting in the formation of an amide linkage. Reaction of a carboxylic acid-functionalized ligand with an amine-bearing conjugation partner, as known in the art, is readily achieved either directly or in the presence of an activated acid such as an acid chloride, acid anhydride, or succinimidyl ester. Reaction of an amine-functionalized ligand with an activated ester, or acid chloride-bearing conjugation partner, as known in the art, is readily achieved.

The preparation of functionalized ligands is illustrated by a ligand in which a methyl ester occupies the $R^5$ position, with all other R-groups being H. An example of such a preparation is one that begins with 1,4,7-triazacyclononane and reacts with dimethylformamide dimethyl acetal to form 1,4,7-triazacyclononane tricyclic orthoamide, which is then reacted with methyl 3,5-dibromolevulinate to form methyl 3,5-bis(4-formyl-1,4,7-triazonan-1-yl)-4-oxopentanoate. The latter is then reacted with sodium borohydride to form methyl 3,5-bis(4-formyl-1,4,7-triazonan-1-yl)-4-hydroxypentanoate, which is then reacted with hydrochloric acid to produce methyl 4-hydroxy-3,5-di(1,4,7-triazonan-1-yl)pentanoate. This sequence of reactions is shown below:

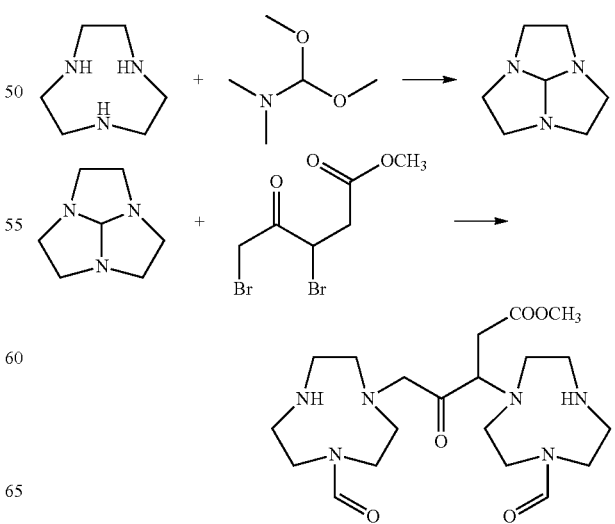

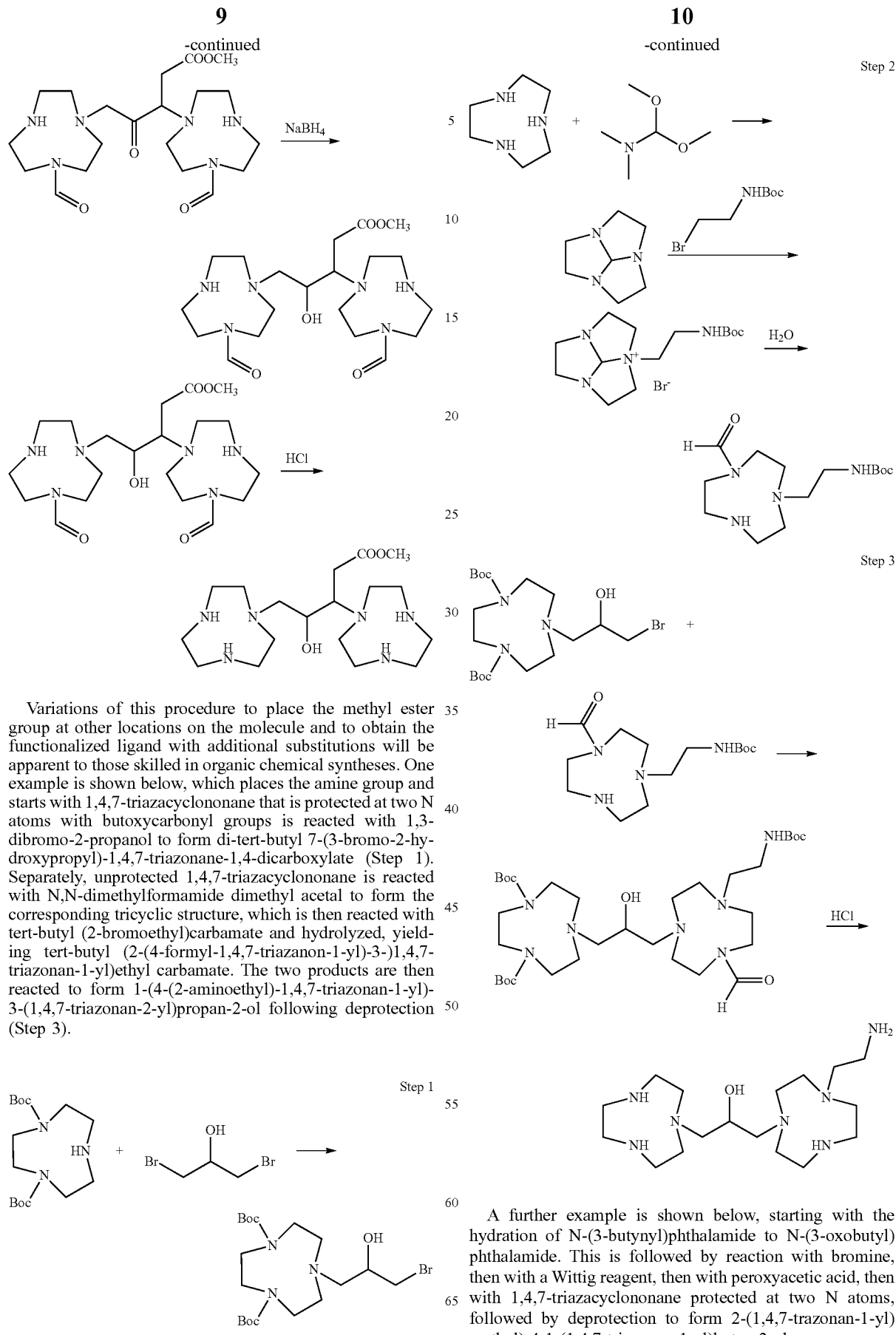

Variations of this procedure to place the methyl ester group at other locations on the molecule and to obtain the functionalized ligand with additional substitutions will be apparent to those skilled in organic chemical syntheses. One example is shown below, which places the amine group and starts with 1,4,7-triazacyclononane that is protected at two N atoms with butoxycarbonyl groups is reacted with 1,3-dibromo-2-propanol to form di-tert-butyl 7-(3-bromo-2-hydroxypropyl)-1,4,7-triazonane-1,4-dicarboxylate (Step 1). Separately, unprotected 1,4,7-triazacyclononane is reacted with N,N-dimethylformamide dimethyl acetal to form the corresponding tricyclic structure, which is then reacted with tert-butyl (2-bromoethyl)carbamate and hydrolyzed, yielding tert-butyl (2-(4-formyl-1,4,7-triazanon-1-yl)-3-)1,4,7-triazonan-1-yl)ethyl carbamate. The two products are then reacted to form 1-(4-(2-aminoethyl)-1,4,7-triazonan-1-yl)-3-(1,4,7-triazonan-2-yl)propan-2-ol following deprotection (Step 3).

A further example is shown below, starting with the hydration of N-(3-butynyl)phthalamide to N-(3-oxobutyl) phthalamide. This is followed by reaction with bromine, then with a Wittig reagent, then with peroxyacetic acid, then with 1,4,7-triazacyclononane protected at two N atoms, followed by deprotection to form 2-(1,4,7-trazonan-1-yl) methyl)-4-1-(1,4,7-triazonan-1-yl)butan-2-ol.

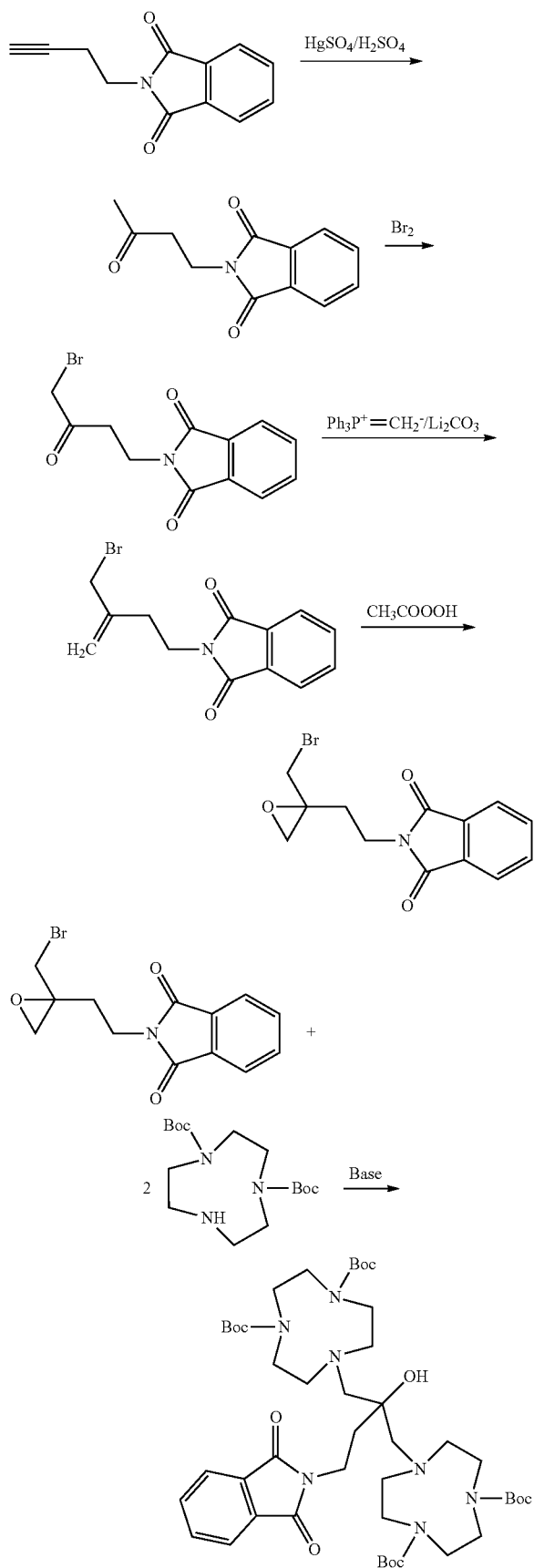

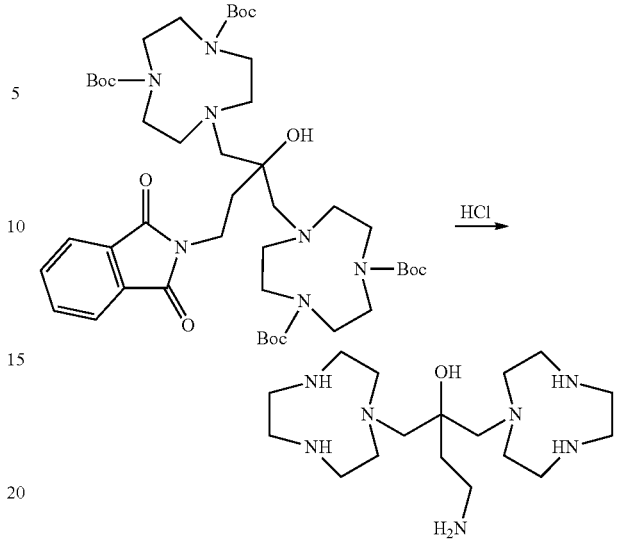

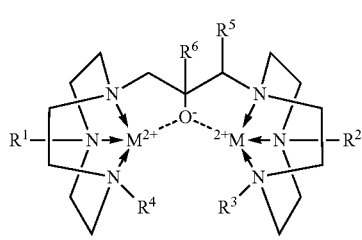

Complexation of either the ligands or the conjugates for use in the present invention can be performed on the ligand, on the functionalized ligand prior to conjugation, or on the conjugate itself. In either case, complexation can be achieved by combining an appropriate salt of the metal, for example $Zn(NO_3)_2$ where a Zn complex is to be formed, with the hydrobromide or hydrochloride salt of the ligand at an appropriate molar ratio, and adjusting the pH to 6.5-7.0.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for the preparation of a separation medium for use in electrophoresis of phosphorylated species, said method comprising polymerizing a monomer mixture comprising acrylamide, a crosslinker, an initiator, and a compound having the formula in which:
one of $R^1$ through $R^6$ is -L-$R^7$ in which L is a member selected from the group consisting of —$CH_2$—C (=O)—NH—($C_1$-$C_4$ alkyl)—, —$CH_2$—C(=O)—NH—($C_1$-$C_4$ alkyl)—NH—, and —($C_1$-$C_4$ alkyl)—NH—, and $R^7$ is an acrylamide group;

the remainder of $R^1$ through $R^6$ are independently selected from the group consisting of H and $C_1$-$C_6$ alkyl; and M is a divalent metal.

2. The method of claim 1 wherein M is a member selected from the group consisting of Ca, Zn, Cr, Mn, Fe, Co, Ni, and Cu.

3. The method of claim 1 wherein M is a member selected from the group consisting of Zn and Mn.

4. The method of claim 1 wherein $R^5$ is -L-$R^7$, and $R^1$, $R^2$, $R^3$, $R^4$, and $R^6$ are independently selected from the group consisting of H and $C_1$-$C_6$ alkyl.

5. The method of claim 1 wherein $R^5$ is -L-$R^7$, and $R^1$, $R^2$, $R^3$, $R^4$, and $R^6$ are H.

6. The method of claim 1 wherein $R^2$ is -L-$R^7$, and $R^1$, $R^3$, $R^4$, $R^5$, and $R^6$ are independently selected from the group consisting of H and $C_1$-$C_6$ alkyl.

7. The method of claim 1 wherein $R^2$ is -L-$R^7$, and $R^1$, $R^3$, $R^4$, $R^5$, and $R^6$ are H.

8. The method of claim 1 wherein $R^6$ is -L-$R^7$, and $R^1$, $R^2$, $R^3$, $R^4$, and $R^5$ are independently selected from the group consisting of H and $C_1$-$C_6$ alkyl.

9. The method of claim 1 wherein $R^6$ is -L-$R^7$, and $R^1$, $R^2$, $R^3$, $R^4$, and $R^5$ are H.

10. The method of claim 1 wherein L is a member selected from the group consisting of —$CH_2$—C(=O)—NH—$CH_2$—$CH_2$—, —$CH_2$—C(=O)—NH—$CH_2$—$CH_2$—NH—, and —$C_2H_5$—NH—.

11. The method of claim 1 wherein $R^5$ is —$CH_2$—C(=O)—NH—$CH_2$—$CH_2$—NH—C(=O)—CH=$CH_2$, and $R^1$, $R^2$, $R^3$, $R^4$, and $R^6$ are H.

12. The method of claim 1 wherein $R^5$ is —$CH_2$—$CH_2$—NH—C(=O)—CH=$CH_2$, and $R^1$, $R^2$, $R^3$, $R^4$, and $R^6$ are H.

13. The method of claim 1 wherein $R^2$ is —$CH_2$—$CH_2$—NH—C(=O)—CH=$CH_2$, and $R^1$, $R^3$, $R^4$, $R^5$, and $R^6$ are H.

14. The method of claim 1 wherein $R^6$ is —$CH_2$—$CH_2$—NH—C(=O)—CH=$CH_2$, and $R^1$, $R^2$, $R^3$, $R^4$, and $R^5$ are H.

* * * * *